United States Patent [19]

Rudis et al.

[11] 4,205,553
[45] Jun. 3, 1980

[54] AUTOMATED GAIN CONTROL IN RAIL FLAW DETECTION

[75] Inventors: Robert P. Rudis, Burlington; Harry L. Ceccon, Boston, both of Mass.

[73] Assignee: The United States of America as represented by the Secretary of the Department of Transporation, Washington, D.C.

[21] Appl. No.: 13,514

[22] Filed: Feb. 21, 1979

[51] Int. Cl.² ............................................ G01N 29/04
[52] U.S. Cl. ........................................ 73/611; 73/615
[58] Field of Search .................. 73/611, 613, 615, 636

[56] References Cited

U.S. PATENT DOCUMENTS

| 4,004,455 | 1/1977 | McKee et al. ........................ 73/615 |
| 4,137,776 | 2/1979 | Rudis et al. ............................ 73/611 |

Primary Examiner—Anthony V. Ciarlante
Attorney, Agent, or Firm—Herbert E. Farmer; Harold P. Deeley, Jr.

[57] ABSTRACT

Automated gain control in rail flaw detection which includes attenuation of echoes from rails pulsed with a burst of sonic energy, comparing said attenuated signals over discrete intervals, and reducing or increasing said attenuation in response thereto to develop a uniform signal from which an evaluation of flaw indicating echoes can be obtained.

3 Claims, 5 Drawing Figures

AGC FUNCTIONAL BLOCK DIAGRAM

ANALOG COMPARATOR

DIGITAL COMPARATOR

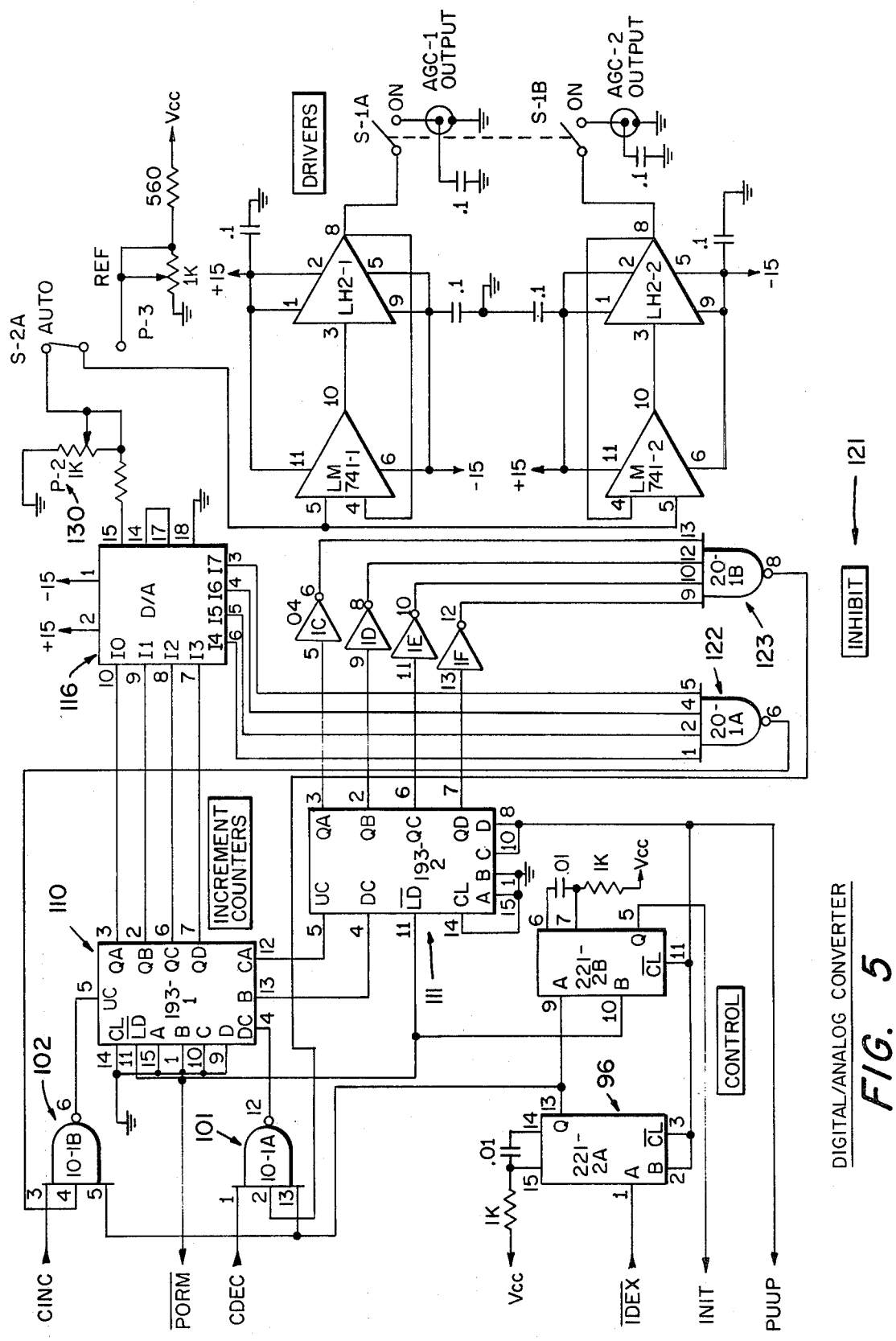

AUTOMATED GAIN CONTROL IN RAIL FLAW DETECTION

ORIGIN OF THE INVENTION

The invention described herein was made by employees of the U.S. Government and may be manufactured and used by, or for, the Government of the United States of America for governmental purposes without the payment of any royalties thereon or therefor.

BACKGROUND OF THE INVENTION

A presently used method of detecting rail flaws is ultrasonic. A quartz crystal is electronically pulsed to generate a burst of oscillations, which signal is applied down through and perpendicular to the top of a rail toward the base from a vehicle passing over the rail rapidly (see U.S. Pat. No. 4,137,776 of the same inventors entitled "Automatic Base Gate Positioning Circuit," issued on Feb. 6, 1979). If a flaw, such as a crack or split, is encountered within the rail, part of the energy of the burst is reflected, with direction of reflection a function of incident angle. The reflected burst is called an echo and is detected through the top of the rail, amplified and subjected to various levels of electronic discrimination. Within the present signal processing systems discrimination consists of a threshold, a D.C. level manually adjusted and set such that background noise is optimally suppressed, which the signal must exceed; and manually set time gates, which when in coincidence with the return signal, determine the region of the rail in which the flaw is located, typically web and base of the rail.

If no flaw is encountered, then reflection of the transmitted signal will occur from the bottom of the rail which is called the base.

In normal operation for a given rail type, using a video screen display of the return amplified and processed signal, the time gates are set and then the base echo signal is adjusted to a predetermined percentage of the video screen height by varying the gain of the active amplifier, assuming all other variables affecting optimization have been properly adjusted. The threshold level is set to exclude noise.

With the equipment set up as described, the test vehicle, which contains the entire flaw detection system, proceeds along the rail. Since the ultrasonic bursts are generated at some distance driven rate, typically 10 bursts/inch of rail, a depth profile along the rail is obtained.

As the detection system moves from rail to rail, however, the base echo reflection in flawless rail may vary in strength primarily because the differing granular structure of various rail will cause more or less attenuation. Another cause of attenuation is top surface contamination of the rail resulting in less efficient transfer of ultrasonic energy into and out of the rail, thereby causing return signal attenuation. Under these circumstances if the echo signal amplitude is altered then a flaw reflection in the same rail will be altered by the same amount. As a result flaws can go undetected or overdetected. The obvious solution is to change the gain of the amplifier to counteract the base echo amplitude variation. In the prior art this is done manually. Since manual response is inherently slow an electronic automatic gain control is needed.

However, some technique must be incorporated within any automatic gain control which takes into account a large number of consecutive base echoes and performs some averaging function on them in order not to be affected by rail flaws or normal rail characteristics such as bolt holes or rail ends.

SUMMARY OF THE INVENTION

The basic function of the automatic gain control of the present invention is, after circuit initialization and calibration, to maintain the pulse amplitude of the base echo between two D.C. threshold values. Whenever the lower threshold is not exceeded or the upper threshold is exceeded for a specified number of cycles the circuit operates to alter the gain of the system amplifier to return the amplitude to within the window, defined by the two threshold values.

Therefore an object of the present invention is to provide an automatic gain control for rail flaw detection.

Another object of the present invention is to provide automatic gain control which averages gain discrete intervals in rail flaw detection.

Another object of the present invention is to provide automatic gain control which discriminates between flaw echoes and rail property echoes in fixing gain.

DESCRIPTION OF THE DRAWINGS

The foregoing objects and many of the attendant advantages of this invention will become more readily appreciated as the same becomes better understood by reference to the following detailed description when taken in conjunction with the accompanying drawings wherein:

FIG. 5 is the digital/analog converter.

Referring to FIG. 1 the basic function of the automatic gain control circuit is, after circuit initialization and calibration, to maintain the pulse amplitude of the base echo between two D.C. threshold values. Whenever the lower threshold 12 is not exceeded or the upper threshold 13 is exceeded for a predetermined number of cycles the circuit operates to alter the gain 30 of the system amplifier to return the amplitude to within the window, defined by the two threshold values.

Figure 1:
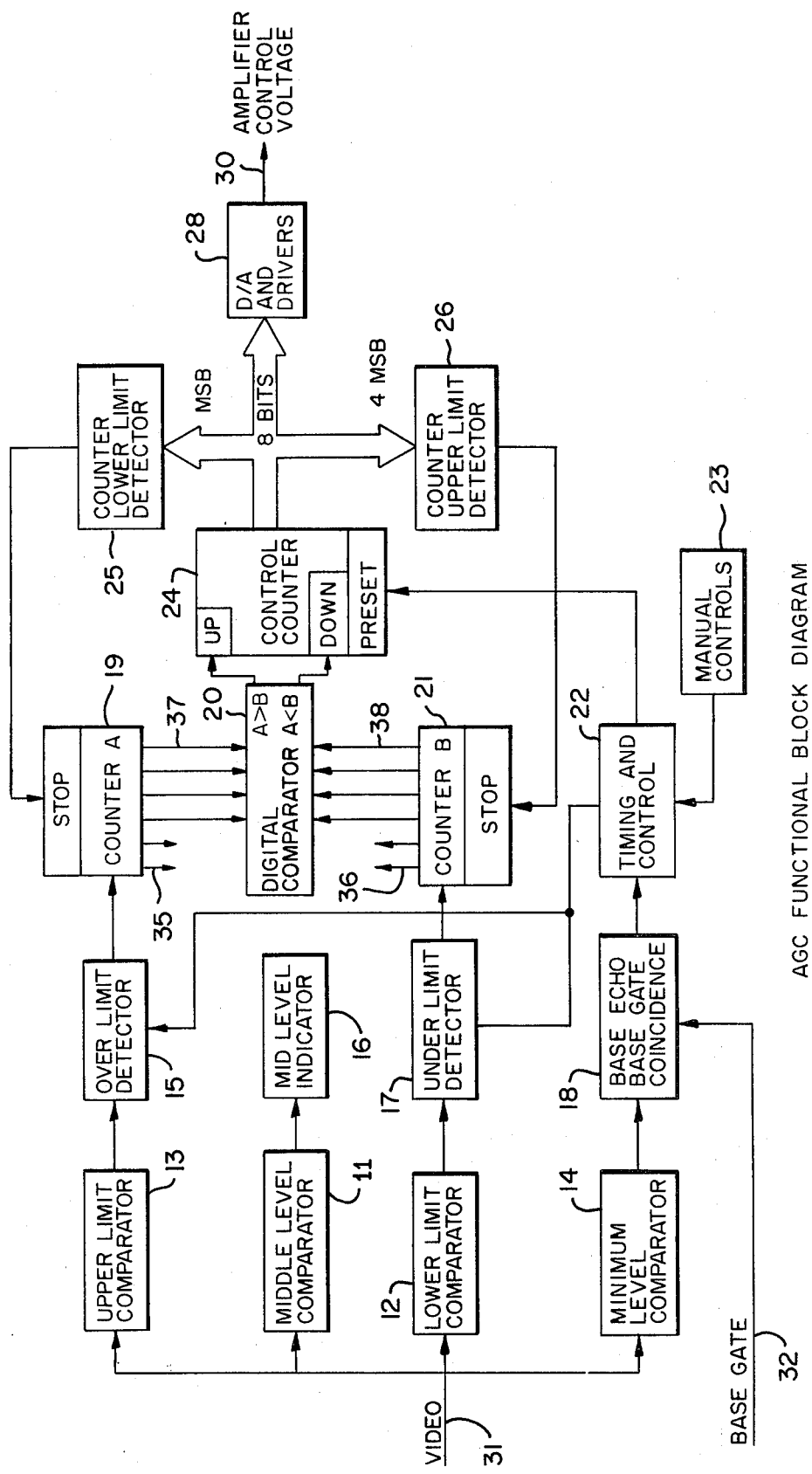
FIG. 1 is a block diagram of the present invention.

At power turn-on initialization of all sequential digital devices occurs. Under manual control 23 all components of the circuit are held in the clear condition except for the middle level comparator 11 and mid-level indicator 16, which is a light emitting diode. In addition the control counter 24 is preset such that the D.C. voltage output 30 of the digital to analog converter 28 is some predetermined value. This fixes the initial gain of the controlled amplifier. Once the amplifier generating the video signal 31 has been externally optimized the desired automatic gain control level is set by adjusting a threshold control until the LED 16 flickers. This now locates the video signal pulse amplitude midway between the upper and lower limits of the window comparator. The window is set nominally for 1 dB range.

Once the AGC level is adjusted comparator threshold levels are set for AGC operation. The minimum level comparator 14 is set such that the dynamic range of the input is nominally 15 dB. For the AGC circuit to recognize a valid input the incoming video signal 31 must have an amplitude greater than nominal 12 dB down from middle level and occur during the base gate 32. Each time these conditions are met (coincidence) an index counter located in the timing and control function 22 increments by one.

If the upper limit comparator 13 threshold is exceeded, Counter A 19, a 6-bit digital counter, is incremented by one. If, however, the video amplitude 31 falls below the lower limit comparator threshold Counter B, 21 also a 6-bit digital counter, is incremented by one.

Once the index counter reaches 32 the four most significant bits 37 and 38 of Counters A and B are compared. The two least significant bits 35 and 36 of Counters A and B are not further processed but are used as a count threshold to help eliminate spurious video amplitude changes.

Depending upon which Counter A or B has the higher count the control counter 24, and 8-bit bi-directional counter, is either decremented or incremented. This in turn alters the value of the D.C. voltage 30 applied to the amplifier gain input through the digital to analog converter 28.

The counter limit detectors 25 and 26 simply define the limit of the Digital/Analog D/A D.C. output voltage excursion 30.

The amplifier control input 30 in this case is assumed to have a gain characteristic of 6 dB volt and full-scale output of the D/A is set at 2.5 volts. By presetting the control counter 24 digital output such that the 8-bit D/A presets at nominally 2.00 volts allows an over-ranging correction of approximately 3 dB and an under-ranging correction of approximately 12 dB. The following table indicates the AGC output range:

TABLE 2.1

| D/A INPUT/OUTPUT STATES | | | |
|---|---|---|---|
| | D/A Input (Binary) 28 LSB | (Decimal) MSB | D/C Output 30 Volts |
| Lower Limit | 1 1 1 1 0 0 0 0 | 15 | 0.156 |
| Preset | 0 0 0 0 0 0 1 1 | 192 | 2.000 |
| Upper Limit | 0 0 0 0 1 1 1 1 | 240 | 2.496 |

There are 177 possible incremental steps to increase gain over the nominal 12 dB range and 48 possible incremental steps to decrease the gain over the nominal 3 dB range.

The automatic gain control has been designed to interface easily with an amplifier of any sonic flaw detection system in which gain control is obtained by first applying a fixed level of attenuation and then reducing the attenuation to cause a gain increase or increasing the attenuation to cause a gain reduction. Based on this the automatic gain control is set to operate from an initial condition of nominal 12 dB of attenuation. From this initial condition a dynamic operating range of 15 dB is available: 12 dB of gain and 3 dB of further attenuation.

The index counter is set to trigger updating of the gain after every 32 ultrasonic cycles. For a distance driven inspection frequency of 10 ultrasonic cycles per inch the gain can be increased or decreased one step every 3.2 inches with each step corresponding to 0.0625 dB. As a result the full range of amplifier attenuation (3 dB) can be implemented over 153.6 inches and the full range of amplifier gain can be implemented over 566.4 inches.

To find the length of the rail, L, over which the full 12 dB of gain may be implemented for different distance driven inspection rates and/or for different cycle counts the following relationship may be used.

$$L = (b/n)(d)$$

where
b = The decimal equivalent for the selected output of the index counter. A power of two.
n = Distance driven inspection rate
d = Number of incremental gain steps
for the present configuration for gain:
b = 32, n = 10, and d = 177
Therefore L = 566.4
For the present configuration for attenuation
b = 32, n = 40 and d = 48
Therefore L = 153.6

OPERATIONAL DESCRIPTION

The automatic gain circuit (AGC) is adaptable to many ultrasonic rail inspection systems since the signals necessary to operate the AGC are normally developed within the ultrasonic system.

The primary requirement is the use of a 0° transducer which generates an ultrasonic burst at some frequency that enters the rail normal to the top surface. The signals necessary are produced during the processing of echo returns from this beam.

Echoes generated within the rail whether from flaws, boltholes, or the base are generally amplified, full wave rectified and smoothed for use within the ultrasonic processing system. The AGC monitors the video returns exceeding a threshold of 2.5 volts and occurring during a base time gate. The reference threshold is 10.0 volts giving a nominal dynamic range of nominally 12 dB.

In order to identify and separate different regions of the rail, typically head, web, and base for individual strip chart channel readout, time gates are generated based on time of occurrence of a rail top detector signal. The position and width of these gates is variable and set according to operational judgment. A base gate is one signal which is used to distinguish base echoes from echoes emanating from other parts of the rail.

Figure 2:
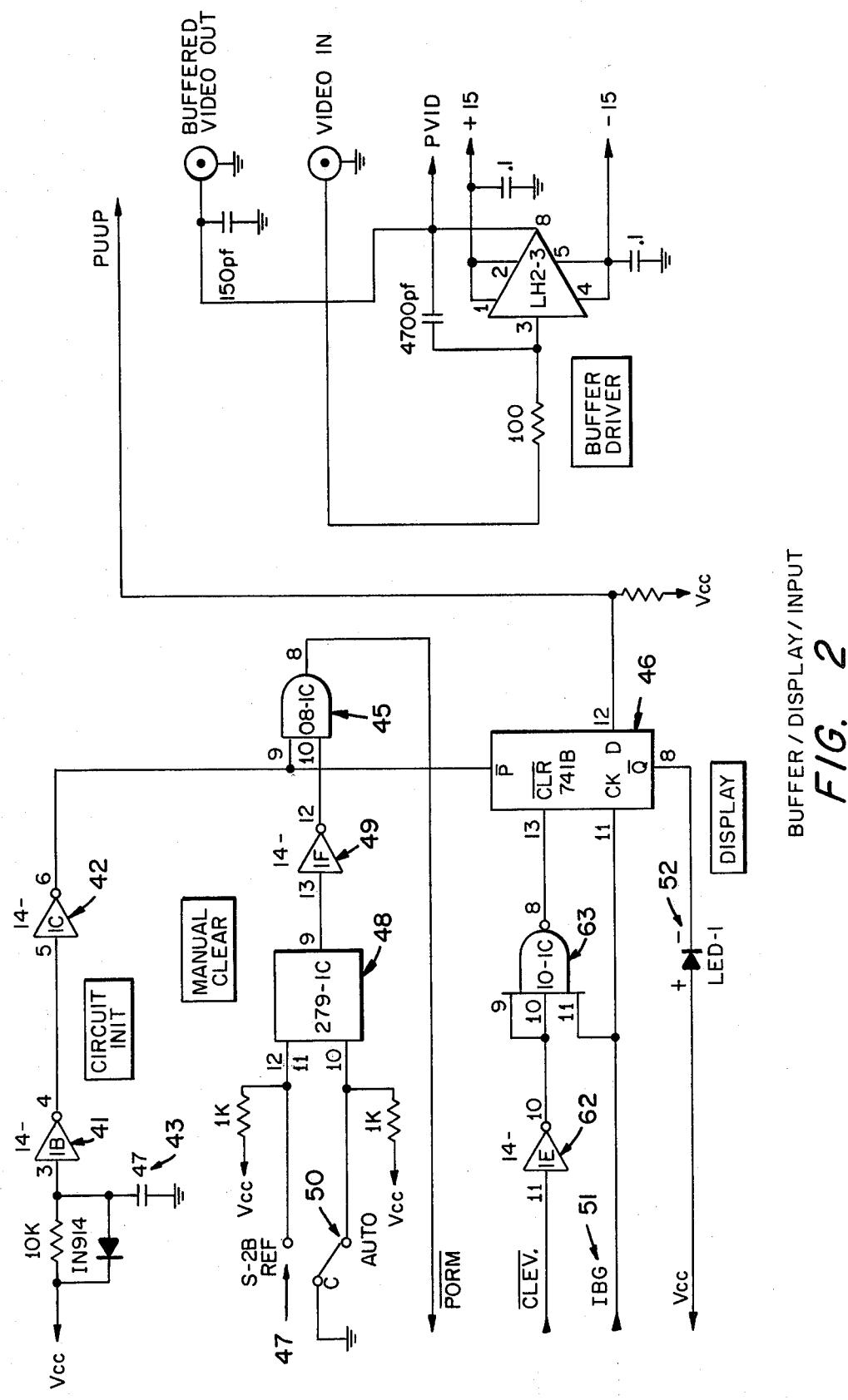
FIG. 2 is the buffer display circuit.

Referring to FIG. 2, circuit initialization takes place through the generation of POWER ON RESET at the output of Inverter 41 and the complement $\overline{POR}$ at the output of Inverter 42. When the power is switched on, the output of 41 is held high and the output of 42 is held low until the capacitor 43 is charged to the threshold level of the Schmitt Inverter 41. The RC time constant is long (>.1 sec.) compared to the settling time of the power at switch-on. Therefore, until the Schmitt threshold is exceeded all sequential and storage components of the circuit are held in the reset or clear condition through Gate 45.

The other input to Gate 45 is used to manually clear and hold in the clear condition all sequential and storage components of the circuit except flip-flop 46.

With a single pole two position switch 47 in the Reference position the output of a latch 48, is held high, inverted through inverter 49 and appears at the output of Gate 45 as $\overline{PORM}$, the clearing signal.

The reference position of Switch 47 is used when the AGC calibration level is to be set or when AGC operation is to be inhibited.

By setting Switch S-2B in the $\overline{AUTO}$ position 50 the output of Gate 45 goes high removing the clear condition and enabling normal AGC operation.

Figure 3:
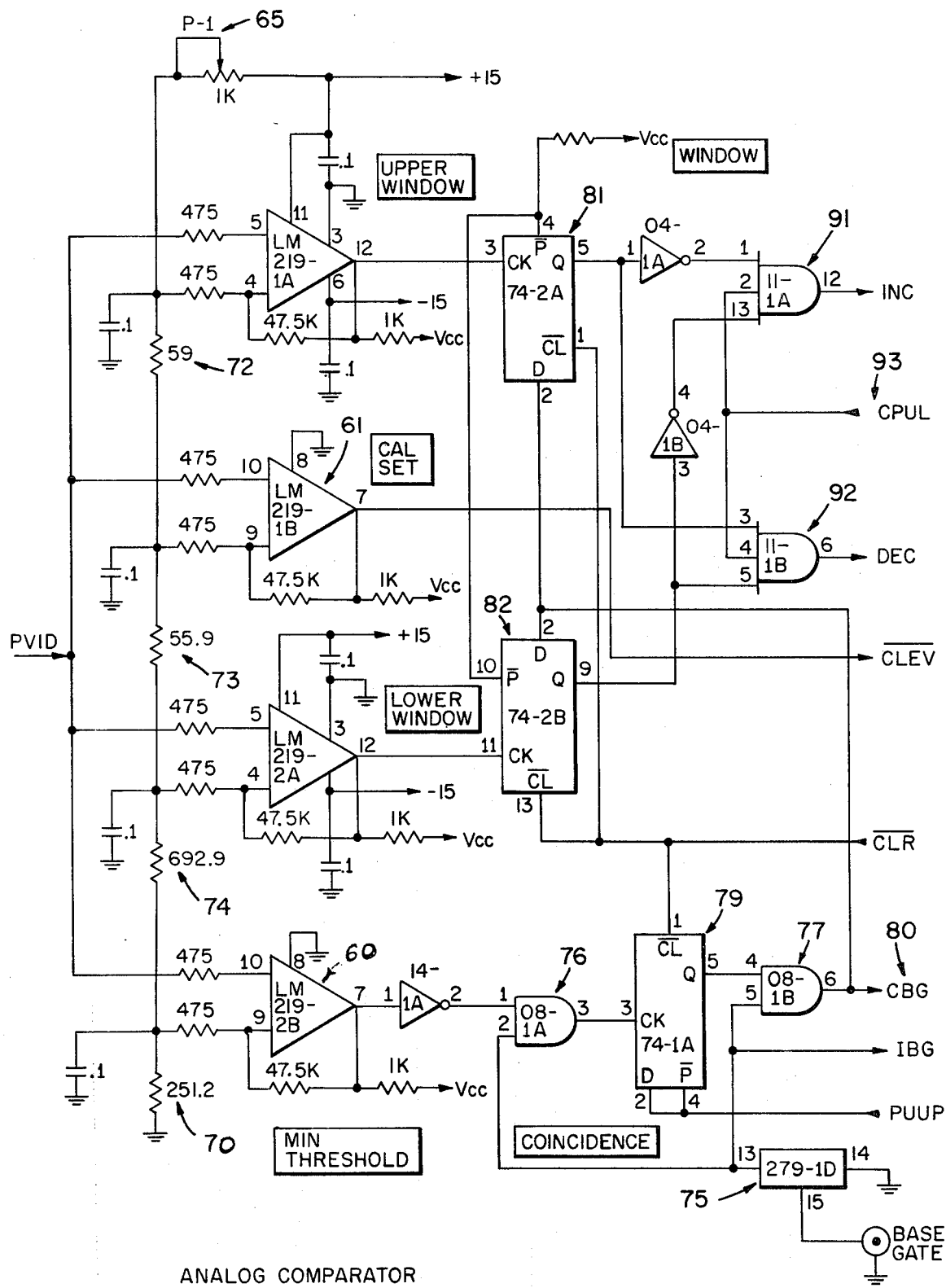
FIG. 3 is the analog comparator.

IBG is the complement of $\overline{\text{BASE GATE}}$ on FIG. 3. On the leading edge of IBG F/F 46 set. As a result the cathode of light emitting diode 52 goes low and the LED is on. However, if during $\overline{\text{BASE GATE}}$, the threshold of Comparator 61 (FIG. 3) is exceeded by a video echo pulse, $\overline{\text{CLEV}}$ is generated. At the output of comparator 61 the F/F 46 is cleared through Inverter 62 and Gate 63 (FIG. 2). This function is used to set AGC calibration level and is carried out by putting switch 47 in the $\overline{\text{REF}}$ position and adjusting potentiometer 65, a front panel control, until the LED just flickers.

If the video signal does not exceed the threshold at comparator 61 or if the echo appears outside $\overline{\text{BASE GATE}}$, $\overline{\text{CLEV}}$ is not generated in the first case and coincidence does not occur at Gate 63 in the later case. As a result the LED stays on.

The circuit Element LH 2-3 is used as a buffer driver between the ultrasonic system amplifier and the comparators in FIG. 3. The output of the buffer is called PVID and is also available for use externally.

The voltage divider which consists of Resistors 70, 74, 73, 72 and Potentiometer 65 having values of 251.2, 692.9, 55.9, 59 and 1K respectively, develop the thresholds for each of the comparators. The values of the fixed resistors were chosen specifically to provide, relative to the reference threshold of comparator 61, an upper window threshold of +0.5 dB, a lower window threshold of −0.5 dB, and a minimum threshold of −12 dB. The voltage values are set by adjusting Potentiometer P-1 to accommodate any desired video amplitude set level between approximately +8 and +15 volts.

$\overline{\text{BASE GATE}}$, is inverted by 75 and applied to the inputs of Gates 76 and 77. A PVID signal, exceeding the threshold of Comparator 60, generates a low true digital signal which is inverted and applied to the other input of Gate 76. If coincidence occurs here the leading edge of the output pulse from Gate 76 sets F/F 79, generating a high on the other input of Gate 77. The output of Gate 77 has a width determined essentially by the leading edge of the digitalized PVID pulse and the trailing edge of $\overline{\text{BASE GATE}}$ and is called CBG 80.

Figure 4:
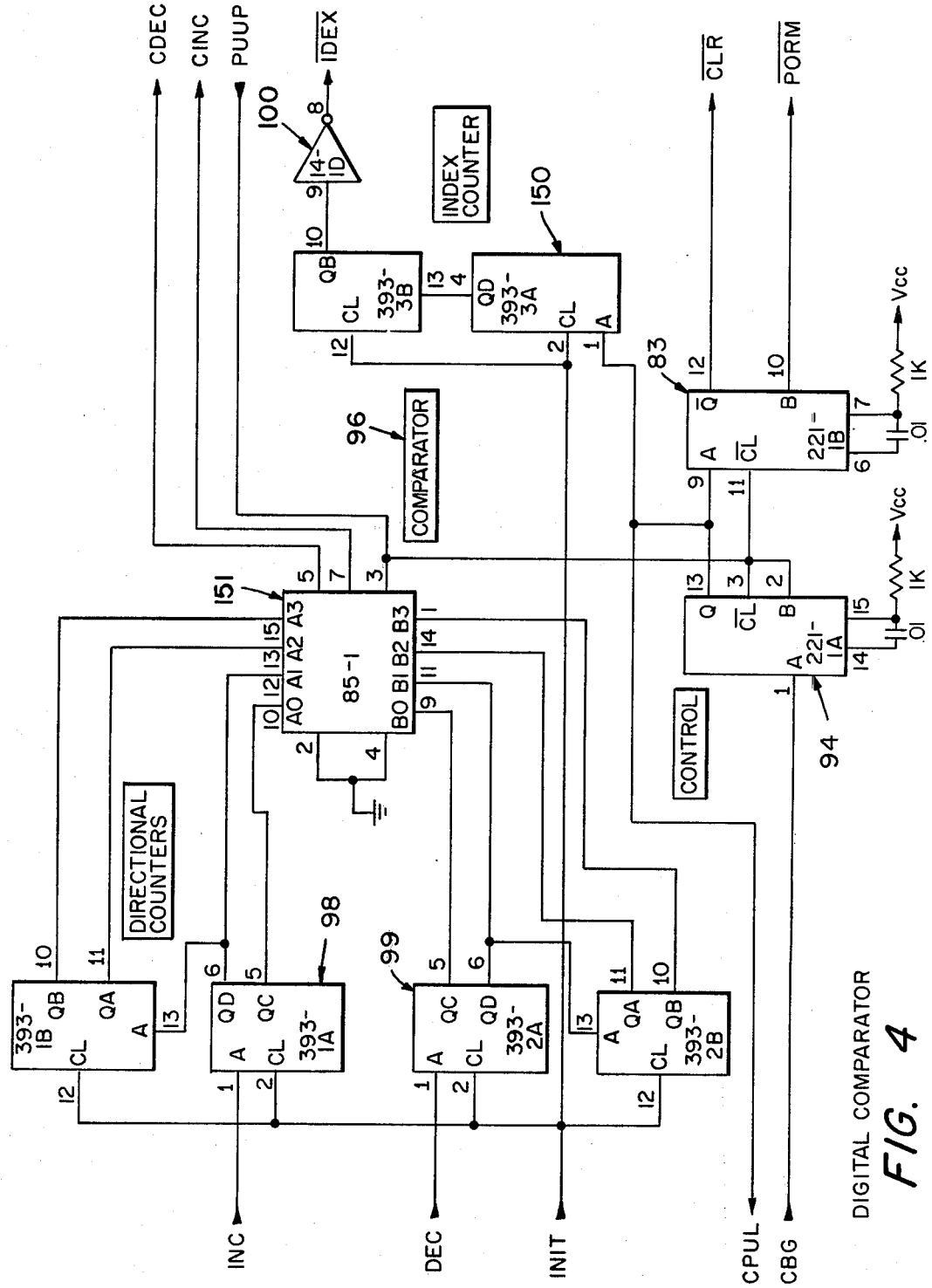
FIG. 4 is the digital comparator.

CBG 80 is applied to the D (data) inputs of F/F's 81 and 82 part of the window circuit and also is used to generate timing and control signals through One-shots 94, 83, FIG. 4.

Without coincidence of the PVID echo and $\overline{\text{BASE GATE}}$ operation of this portion of the circuit is not enabled. This decision is made at Gate 76. Assuming PVID echo and $\overline{\text{BASE GATE}}$ coincidence and the threshold of Comparator 60 has been exceeded, the D inputs of F/F's 81, and 82, have been conditioned high. If the PVID signal exceeds the threshold for the lower window comparator then on the *trailing* edge of the digitalized PVID F/F 82 is set transferring the high on the D input on the Q output. If the upper window threshold is exceeded then F/F 81 is affected similarly. The output states of these flip/flops provide the logic which determines how, if at all, the ultrasonic system amplifier gain should be adjusted.

The following table gives all the possible states of the two flip/flops and following is a discussion of the consequences of each state.

| WINDOW COMPARATOR LOGIC STATES | | | | |
|---|---|---|---|---|
| Upper Window (81) | L | H | L | H |
| Lower Window (82) | L | L | H | H |

-continued

| WINDOW COMPARATOR LOGIC STATES | | | | |
|---|---|---|---|---|
| State Number | 1 | 2 | 3 | 4 |

State 1 indicates that the PVID echo amplitude is below the lower window threshold and gain should be increased. Two of the input lines of Gate 91 are high. CPUL 93, which is generated through One-Shot 94 FIG. 4 on the trailing edge of CBG now passes through Gate 91 to the Digital Comparator (FIG. 4) circuit as INC.

State 2 is logically impossible since it indicates the upper window threshold was exceeded but the lower window threshold was not.

State 3 indicates that the PVID echo signal is within the window.

State 4 indicates both window limit thresholds have been exceeded. This situation causes Gate 92 to be enabled and pulse CPUL 93 passes through and becomes DEC. This signal is applied to the Digital Comparator (FIG. 4).

As stated previously an echo exceeding the minimum threshold and occurring during $\overline{\text{BASE GATE}}$ generates CBG, which among other things, on its trailing edge, generates CPUL through a One-Shot 94. If neither flip/flop 81 or 82 is set then CPUL becomes INC through Gate 91 and on its trailing edge increments Counter 98 by one. Alternatively, if both flip/flops are set then CPUL becomes DEC through Gate 92 and on its trailing edge increments Counter 99.

The counters 98, 99 are wired as 6-bit counters with only the four most significant bits of each compared to one another in the Digital Comparator (FIG. 4).

The index counter 150 incremented on the trailing edge of CPUL determines the number of ultrasonic cycles to be considered before any new instructions for whether the gain is to be increased or decreased are implemented.

The output of the Index Counter, $\overline{\text{IDEX}}$ through Inverter 100, is wired to be true every 32 ultrasonic cycles. The leading edge of $\overline{\text{IDEX}}$ is used to trigger One-Shot 96 to generate control pulse for operation of DAC FIG. 5.

The four most significant bits of the directional counters are compared in 151. If $\text{INC}_{TOTAL} > \text{DEC}_{TOTAL}$ then CDEC goes high and transfers information to Gate 101 in DAC FIG. 5. If $\text{DEC}_{TOTAL} > \text{INC}_{TOTAL}$ then CINC goes high and transfers information to Gate 102 in DAC FIG. 5.

In order to clear the appropriate circuit elements for operation in the next cycle a signal called $\overline{\text{CLR}}$ is generated at One-Shot 83. This signal is operated on the trailing edge of CPUL or the trailing edge of $\overline{\text{PORM}}$ from Gate 45 in FIG. 2. However, while $\overline{\text{PORM}}$ is true, when 47 is in the $\overline{\text{REF}}$ position, generation of $\overline{\text{CLR}}$ is inhibited so that coupled with the effects on DAC FIG. 5, the circuit is inhibited from operating automatically.

When $\overline{\text{IDEX}}$ goes true the leading edge triggers One-shot 96. The output pulse appears on input lines of both gates 102 and 101. If either CINC or CDEC is high and if the corresponding input from INHIBIT is high then Counter 110 will be incremented if CINC is high and decremented if CDEC is high.

Counters 110 and 111 are loaded with a decimal count of 192 upon initialization ($\overline{\text{POR}}$) and are loaded and held there when switch 47 is in the $\overline{\text{REF}}$ position through $\overline{\text{PORM}}$.

This count forces on output DC voltage of 2 volts through the digital to analog converter 116. By the defined characteristics of the ultrasonic system amplifier discussed previously this represents 12 dB of attenuation. As counter 110 and 111 are decremented the DC voltage falls and less attenuation or, equivalently, more gain is applied to the aplifiers. If the counters are incremented then more attenuation is applied.

The INHIBIT 121 function is used to limit the excursion of the Counters 110 and 111 which are bi-directional.

The four most significant bits of the 8-bit output of the counters are sampled by Gates 122 and 123. The output of 122 goes low when all four inputs are high and as a result inhibits CINC Gate 102. This limits the maximum count of the increment counters to 240 decimal. Gate 123 on the other hand, monitors the inverted outputs of the Counter 111. When these outputs are all low the output of 123 goes low and inhibits CDEC Gate 101. The lower limit of the counters, as a result, is 15 decimal.

The Digital/Analog Converter 116 is an 8-bit device with an output voltage range of zero to ten volts.

A voltage divider of which Potentiometer 130 is a part, is used to reduce the D/A output voltage to the values given below.

| | D/A OUTPUT RANGE | | |
|---|---|---|---|
| | D/A Input Value Decimal | Output Voltage S-2A (C) | Gain dB |
| | 15 | .16 | .94 |
| REF | 192 | 2.00 | 12 |
| | 240 | 2.50 | 15 |

This table represent the range over which the control works. In the $\overline{\text{REF}}$ position of Switch 47 the voltage should be 2.00.

The foregoing circuits describe very specific apparatus. Many substitutions and variations may be made in these circuits without departing from the true scope and spirit of our invention. We therefore wish to be limited only by the appended claims.

We claim:

1. Automated gain control in rail flaw detection comprising:
   means for amplifying ultrasonic echo signals from rails;
   means for attenuating said amplified signals a predetermined amount;
   means for changing said attenuation by discrete amounts;
   means for detecting amplitude variations beyond a predetermined level;
   means for detecting amplitude variations a prescribed amount below a predetermined level;
   means for counting the number of excursions above said predetermined level over a preselected interval;
   means for counting the number of said excursions below said predetermined level; and
   means for comparing the counts above and below said predetermined level whereby attenuation of said amplified signal is changed a discrete amount according to the number of excursions above or below said predetermined level.

2. The apparatus as defined in claim 1 which further includes means for reducing the effect of spurious returns on the amplification of the signals.

3. The apparatus as defined in claim 1 which further includes means for reducing the effect of spurious returns on the attenuation of the signals.

* * * * *